United States Patent [19]

Morii

[11] Patent Number: 4,802,369

[45] Date of Patent: Feb. 7, 1989

[54] SENSOR STRUCTURE

[75] Inventor: Hiroaki Morii, Aichi, Japan

[73] Assignee: NGK Spark Plug Co., Ltd., Aichi, Japan

[21] Appl. No.: 76,578

[22] Filed: Jul. 22, 1987

[30] Foreign Application Priority Data

Jul. 22, 1986 [JP] Japan .................. 61-172466

[51] Int. Cl.$^4$ .................................. G01N 27/26
[52] U.S. Cl. ...................... 73/116; 204/424
[58] Field of Search ............... 73/116, 118.1, 119 R; 123/440, 489; 29/595; 60/276; 204/421, 424, 425, 426, 428, 429

[56] References Cited

U.S. PATENT DOCUMENTS

| 4,123,131 | 10/1978 | Pearce, Jr. et al. | 204/428 |
| 4,560,463 | 12/1985 | Frey et al. | 204/424 |
| 4,569,748 | 2/1986 | Yamakawa et al. | 204/427 |
| 4,591,423 | 5/1986 | Kato et al. | 204/428 |
| 4,597,849 | 7/1986 | Burkhardt et al. | 204/424 |
| 4,624,770 | 11/1986 | Yamada et al. | 204/428 |

Primary Examiner—Stewart J. Levy
Assistant Examiner—Robert R. Raevis
Attorney, Agent, or Firm—Sughrue, Mion, Zinn, Macpeak & Seas

[57] ABSTRACT

A sensor structure including a ceramic detecting element mounted in a metal sleeve through an insulator, the metal sleeve being fixed to a main metal tubular member through heat-sealing, and the metal sleeve is sealed. Due to the use of the metal sleeve, splitting and cracking are eliminated, always maintaining good airtightness and protecting the sensor from damage.

7 Claims, 4 Drawing Sheets

SENSOR STRUCTURE

BACKGROUND OF THE INVENTION

The present invention relates to the structure of a sensor, for example, an air-fuel ratio sensor for detecting the concentration of oxygen density using as a detecting element a ceramic solid electrolyte.

To construct a sensor for detecting conditions of the ambient atmosphere and producing an electrical signal indicative of the detected parameters, for example, an air-fuel ratio sensor, a structure as shown in a partial cutaway view of FIG. 1 has been proposed. FIG. 2 is a perspective view showing a ceramic sleeve 54a used in the sensor structure of FIG. 1, and FIG. 3 is a perspective view showing a ceramic guide 50ax used in the same sensor structure.

A ceramic detecting element 14a fixed to ceramic guides 50ax and 50ay through cement 52a is held in the ceramic sleeve 60a through which lead wires 2 pass in an insulated state. Seal members 19a and 20a are provided on the side of a base portion 17ay of the ceramic sleeve 54a. After the space therebetween is filled with talc powder 58a, the ceramic sleeve 54a and a cylindrical main metal tubular member 24a are heat-sealed to fix them together. At the same time, a metal outer cylinder 28a, disposed against the outside of the ceramic sleeve 54a and on the side of the base portion 17ay on which a flange portion of the ceramic sleeve 54a is provided, is simultaneously heat-sealed. A protective outer cylinder 32a externally touching the metal outer cylinder 28a is sealed by heating along six directions.

In this proposed sensor 4a structure, however, the ceramic detecting element 14a is fixed in the ceramic sleeve 54a through the glass 18a and cement 52a, 56ax, and 56ay. Accordingly, problems arise in that splits or cracks often occur in the ceramic sleeve 54a when the ceramic sleeve 54a is externally sealed, thereby giving rise to difficulties relating to the sealing property and allowing for the possibility of damage in the internal structure of the sensor 4a.

SUMMARY OF THE INVENTION

In order to solve the problems described above, the present invention provides a sensor structure comprising:
 a quadrangular prism detecting element made of ceramics;
 a metal sleeve having a through hole in which the ceramic detecting element is fitted through an insulator;
 a seal member for closing the through hole of the metal sleeve; and
 a main metal tubular member integrally provided with the metal sleeve in the inside thereof.

The ceramic detecting element may be a detecting element made of, for example, $ZrO_2$, which is a solid electrolyte, and the insulator may be an insulating porcelain tube for holding the ceramic detecting element in the through hole. The metal sleeve may be made of SUS-403, 304, 430, or 310 stainless steel, and the seal member may be made of lead glass or glass of a boric acid group, or it may be constituted by three layers, namely, a glass layer, a fluorine rubber layer, and a silicone rubber layer, arranged in the stated order from a top end side of the metal sleeve. Further, the main metal tubular member may be made of SUS-403 stainless steel.

The through hole of the metal sleeve is blocked by the seal member so that airtightness from one opening portion to the other opening portion can be maintained. The metal sleeve is integrally provided inside the main metal tubular member so that the metal sleeve acts as a shock absorber to thereby protect the ceramic detecting element when the internal structure of the sensor is formed. Further, the ceramic detecting element is mounted in the through hole of the metal sleeve through the insulator, so that the ceramic detecting element can be maintained in an insulated state.

DESCRIPTION OF THE PREFERRED EMBODIMENTS

Figure 1:
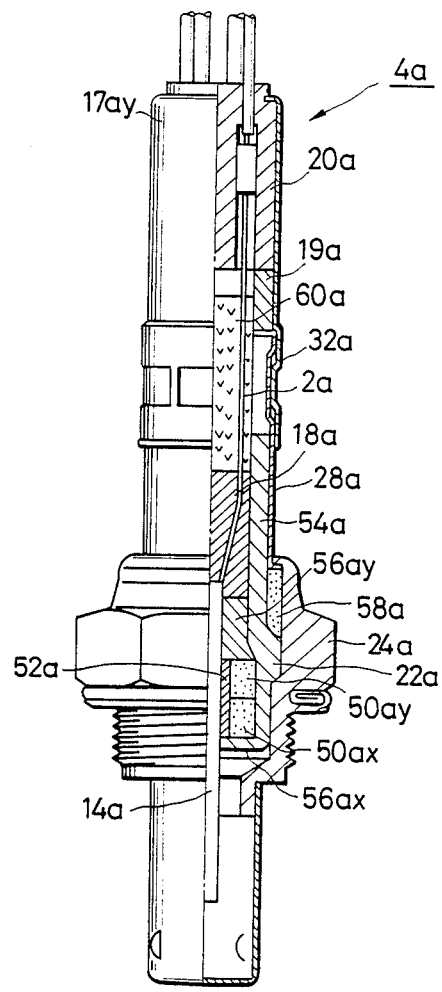
FIG. 1 is a partial cutaway view showing a proposed sensor structure.
Figure 2:
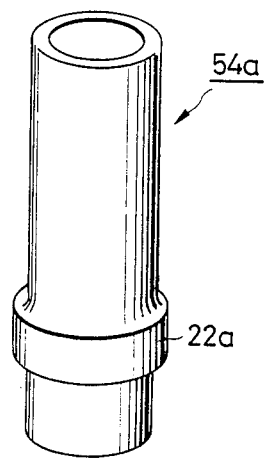
FIG. 2 is a perspective view of a ceramic sleeve.
Figure 3:
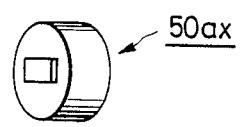
FIG. 3 is a perspective view of a ceramic guide.

Referring to the drawings, preferred embodiments of the sensor structure according to the present invention will be described hereunder.

Figure 4A:
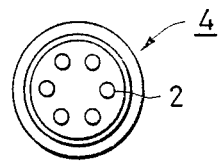
FIG. 4(a) is a plan view showing the arrangement of lead wires in a first embodiment of a sensor structure of the present invention.
Figure 4B:
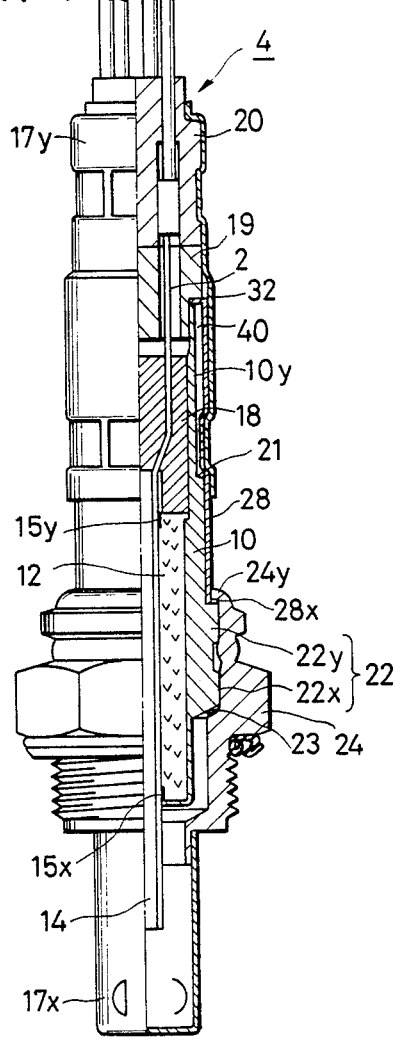
FIG. 4(b) is a partial cutaway view of the same.
Figure 5:
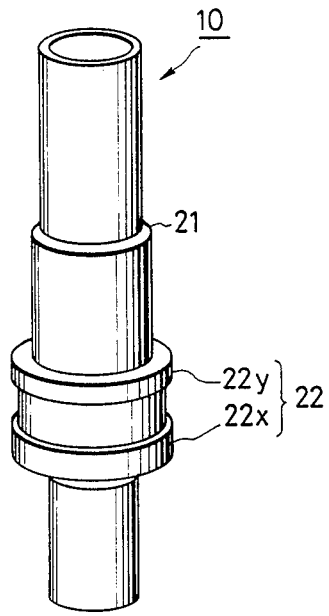
FIG. 5 is a perspective view showing a metal sleeve.
Figure 6:
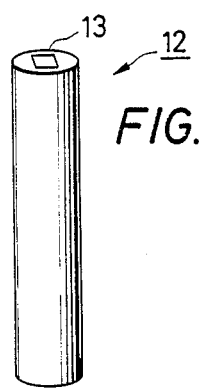
FIG. 6 is a perspective view showing an insulating porcelain tube.

FIGS. 4(a) and 4(b) show a first embodiment of a sensor structure according to the present invention, of which FIG. 4(a) is a plan view showing an arrangement of lead wires 2, and FIG. 4(b) is a partially cutaway view showing a sensor 4. FIG. 5 is a perspective view showing a metal sleeve 10, and FIG. 6 is a perspective view showing an insulating porcelain tube 12.

Figure 7:
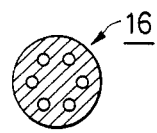
FIG. 7 is a cross-section of a seal member.

The cylindrical insulating porcelain tube 12, which is made of alumina and has a rectangular through hole 13 at its central portion, internally touches the metal sleeve 10, which is made of SUS-403 stainless steel. A ceramic detecting element 14 such as an air/fuel ratio sensing element in the form of a quadrangular prism as a whole formed by piling up ceramic layers (for example, an air/fuel ratio sensing element shown in the Japanese Patent Application No. 32496/1986, the U.S. patent application Ser. No. 912,462 or the West German Patent Application P36 32 456.6) is inserted through the through hole 13 of the insulating porcelain tube 12 and is fixed by cement 15x and 15y in the vicinity of both open ends at a top portion 17x and a base portion 17y of the through hole 13 of the insulating porcelain tube 12. On the side of the base portion 17y, the respective end surfaces of the insulating porcelain tube 12 and the ceramic detecting element 14 are blocked by glass 18, fluorine rubber 19, and silicone rubber 20, in stated order from the end surface side, and the lead wires 2 are extended from the ceramic detecting element 14 through the three layer seal members. Lead glass or glass of a boric acid group may be used as the glass of the glass layer seal member. FIG. 7 shows a cross-section of the glass layer.

Figure 8:
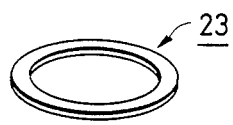
FIG. 8 is a perspective view of a metal packing.

A flange portion 22 is provided around the entire outer circumferential wall of the metal sleeve 10 at its central portion, the flange portion 22 being constituted by two flange portions 22x and 22y. A main metal tubular member 24 touching the two flange portions 22x and 22y at their outer peripheries and made of SUS-403 stainless steel is fixed to the metal sleeve 10 through heat-sealing. A circular metal packing 23 of SUS-403 stainless steel having a thickness of about 0.3 mm and shown in a perspective view in FIG. 8 is provided between a side wall surface of the flange portion 22x on the side of the top portion 17x and the main metal tubular member 24.

Figure 9:
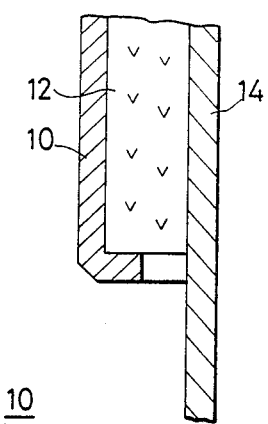
FIG. 9 shows a cross-section in the vicinity of a base portion of the metal sleeve.

The metal sleeve 10 extending from the flange portion 22 towards the top portion 17x is made thin to reduce its weight. The top end of the metal sleeve 10 is bent inward by 90 degrees so as to hold the insulating porcelain tube 12 through which the ceramic detecting element 14 passes, as shown in partial cross-section in FIG. 9.

Figure 10:
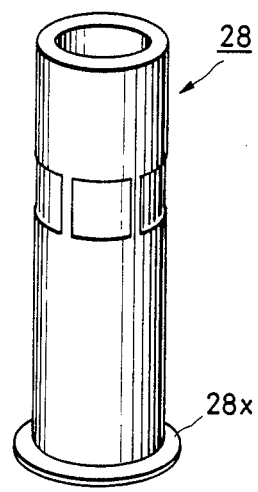
FIG. 10 is a perspective view of a metal tube.

A thin metal outer tube 28 having an end portion 28x on the side of the top portion 17x and bent outward by 90 degrees as shown in perspective view in FIG. 10 touches the outer circumferential wall of the metal sleeve 10 on the side of the base portion 17y from the flange portion 22, and further extends towards the base portion 17y. In heat-sealing, the end portion 28x of the metal tube 28 is placed at the inside of the end portion 24y of the main metal tubular member 24 on the side of the base portion 17y so as to be heat-sealed thereto. Further, a protective outer tube 32 touches the outer circumferential wall of the metal outer tube 28 on the side of the base portion 17y and is hexagonally sealed at the touching portion.

Figure 11:
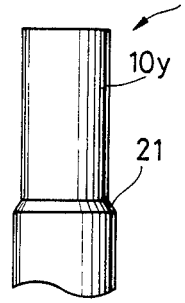
FIG. 11 is a front view showing an end portion of the metal sleeve on the base portion side.
Figure 12:
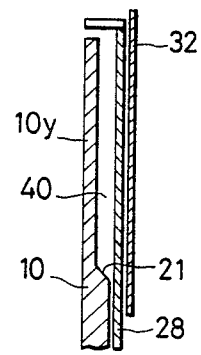
FIG. 12 is an end view showing the end portion of the metal sleeve.

In the embodiment described above, the metal sleeve 10 is provided with a step portion 21 having a height of about 0.5 mm and made thin as shown in FIG. 11, which is a front view showing an end portion 10y of the metal sleeve 10 on the side of the base portion 17y, and as shown in FIG. 12, which is an end view showing the circumference of the end portion 10y, so that the step portion 21 is effective in absorbing external impacts. An air layer 40 is formed between the end portion 10y of the metal sleeve 10 on the side of the base portion 17y and the metal outer tube 28 to obtain an adiabatic effect and so as to reduce the effects of externally generated heat.

The use of the metal sleeve 10 is effective in preventing generation of splits or cracks due to the heat sealing and is further advantageous in that the metal sleeve 10 can be easily worked, compared with a ceramic sleeve, to various shapes which provide an improved performance of the sensor 4. As described above, the metal sleeve 10, the main metal tubular member 24, and the metal packing 23 are made of the same material so that they have the same thermal expansion coefficient.

These members also have substantially the same thermal expansion coefficient as the detecting element 14 which is made of ceramic zirconia solid electrolyte. Accordingly, reduction in the measuring accuracy of the sensor 4 is prevented because the airtightness of the device will always be maintained since cracking due to differences in thermal expansion coefficients cannot occur.

In the conventional sensor structure, it was found that there was gas leakage of 40 through 60 cc per minute at an air pressure of 15 kg/cm$^2$. In the first embodiment according to the present invention, on the contrary, the gas leakage is too little to be measured due to the feature of substantially the same thermal expansion coefficients being present among the various constituent members, as described above, and due to the seal materials. Hence, a remarkably good airtightness is maintained. The use of fluorine rubber as the seal material provides a heat-resistant effect, and the use of inexpensive silicone rubber 20 is effective in reducing costs because the temperature of the lead wires 2 is not higher than 200° C. on the side of the base portion 17y of the seal members, thus enabling silicone rubber 20 to be used.

Figure 13A:
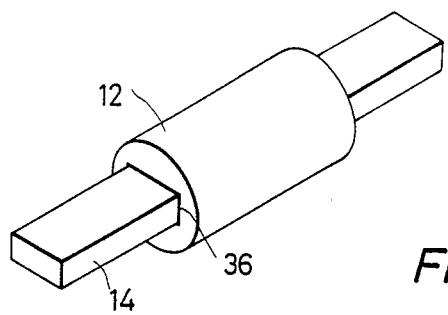
FIG. 13(a) shows in a perspective view a fixing state of a single insulating porcelain tube.
Figure 13B:
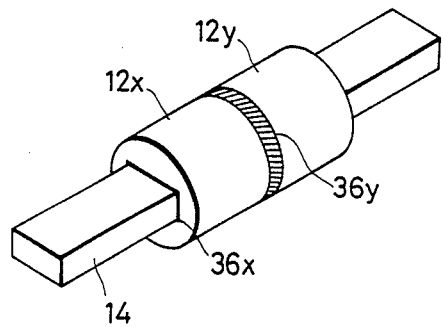
FIG. 13(b) shows a perspective view of a fixing state of two insulating porcelain tubes.

In the above-described embodiment, talc powder (58a in FIG. 1) is not used, and hence the step for talc powder is not required, thereby reducing the number of steps required in manufacturing the sensor 4. Further, the insulating porcelain tube 12 through which the ceramic detecting element 14 passes can be easily assembled by insertion into the metal sleeve 10, and thus there is the further advantage that the manufacturing process is quite easy. The insulating porcelain tube 12 may be constituted by a single unit fixed with cement 36 at the circumference of the opening thereof, as shown in perspective view of FIG. 13(a), while, alternatively, it may be constituted by two insulating porcelain tubes 12x and 12y fixed with cement 36x and 36y, as shown in FIG. 13(b). Particularly in the case where two (or more) insulating porcelain tubes are used, as each tube has an opening at each end (before cementing), four (or more) openings are provided to increase the fixing area. As a result, the strength of attachment is improved.

Figure 14A:
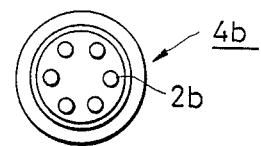
FIG. 14(a) shows in a plan view an arrangement of leads in a second embodiment of the present invention.
Figure 14B:
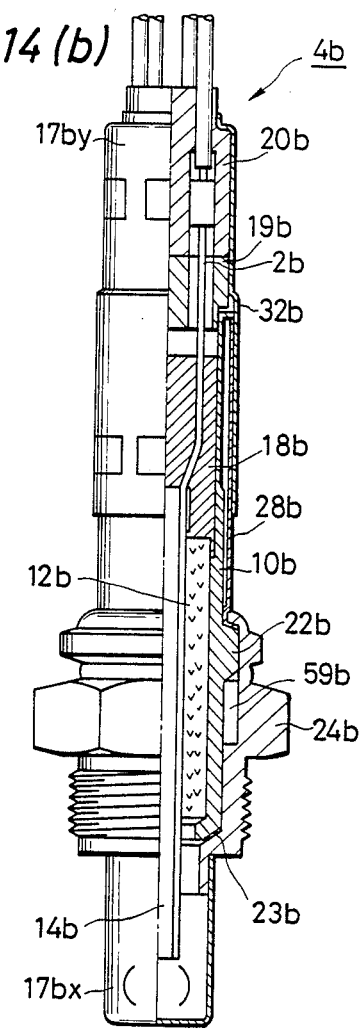
FIG. 14(b) is a partial cutaway view of the same.

FIGS. 14(a) and 14(b) show the structure of a second embodiment of the sensor 4b according to the present invention, of which FIG. 14(a) is a plan view showing an arrangement of lead wires 2b of the sensor 4b and FIG. 14(b) is a partially cutaway view of the same.

In the second embodiment, the inner diameter of a metal sleeve 10b is made larger to reduce the weight of the sleeve as compared to the sleeve of the first embodiment, and the shape of the metal sleeve 10 on the side of a top portion 17bx as well as the shape of a metal packing 23b are different from their shapes in the first embodiment. A ceramic detecting element 14b is mounted in the metal sleeve 10b through an insulating porcelain tube 12b internally touching the metal sleeve 10b and is fixed to a main metal tubular member 24b by heat-sealing. A metal outer tube 28b and a protective outer tube 32b are provided outside the metal sleeve 10b on the side of its base portion 17by. Glass 18b, fluorine rubber 19b, and silicone rubber 20b are used as seal members, and the lead wires 2b extend through the seal members. A flange portion 22b is formed on the outer circumferential wall of the metal sleeve 10b at its central portion and is fixed to the main metal tubular member 24 by heat-sealing. A space 59b is formed between the metal sleeve 10b extending toward the top portion 17bx from the flange portion 22b and the main metal tubular member 24b; however, airtightness is maintained because one end of the metal sleeve 10b is bent inward and the metal packing 23b is closely provided between the outer wall of the bent metal sleeve 10b portion and the main metal tubular member 24b. Because sealing is performed by the metal packing 23b at the top end of the metal sleeve 10b, the internal volume from the portion to be sealed to the top end of the ceramic detecting element 14b is reduced, and hence the flow of the gas to be measured is facilitated, thereby improving the responsiveness of the sensor 4b. There is such a further advantage in that the manufacture of the device is facilitated owing to the simple shape of the metal sleeve 10 on the side of the top portion.

In the sensor structure according to the present invention, a ceramic detecting element is mounted in a metal sleeve through an insulator, the metal sleeve is fixed to a main metal tubular member by heat-sealing, and the metal sleeve is sealed. In this sensor structure, because of the use of the metal sleeve, splitting and cracking are eliminated, even if the metal sleeve and the main metal tubular member are fixed by heat-sealing. The airtightness of the device is thereby maintained, and the sensor structure is protected from damage. Further, the metal sleeve can be easily worked into a complicated shape, providing the advantage that any desired shape of the metal sleeve can easily be obtained. There is a further advantage that if the glass acting as the seal member is selected to have substantially the same thermal expansion coefficient as the metal sleeve, the airtightness as well as the measuring accuracy of the sensor can be still further improved.

What is claimed:

1. A sensor structure comprising:
   a quadrangular prism-shaped detecting element (14) made of a ceramic material;
   a metal sleeve (10) having a through hole in which said ceramic detecting element is disposed;
   a seal member (18-20) for closing said through hole of said metal sleeve;
   a main metal tubular member (24) integrally provided with said metal sleeve in the inside thereof; and
   a metal outer tube (28) fixed to an outer circumferential wall of said metal sleeve, wherein an outer diameter of said metal sleeve is step-wise reduced for forming an air layer (40) between a reduced portion (10y) of an outer diameter of said metal sleeve and said metal outer tube.

2. The sensor structure according to claim 1, in which said metal sleeve is made of SUS stainless steel.

3. The sensor structure to claim 1, in which said seal member is made of at least glass.

4. The sensor structure according to claim 1, in which said seal member comprises at least three layers comprising a glass layer, a fluorine rubber layer, and a silicone rubber layer, disposed in the stated order from a top end of sand metal sleeve.

5. The sensor structure according to claim 1, further comprising an insulator having a through hole, said insulator being fitted in said through hole in said metal sleeve, and said ceramic detecting element being fitted in said through hole in said insulator.

6. The sensor structure according to claim 5, in which said insulator comprises a cylindrical insulating tube member, and said through hole is rectangular and is provided at a central portion of the tube member.

7. The sensor structure according to claim 6, in which said insulator comprises a plurality of cylindrical insulating tube members fixed with one another.

* * * * *